United States Patent
Rudolf et al.

(10) Patent No.: US 12,049,458 B2
(45) Date of Patent: *Jul. 30, 2024

(54) THIOCARBONATE COMPOUNDS

(71) Applicant: BASF SE, Ludwigshafen am Rhein (DE)

(72) Inventors: Peter Rudolf, Ludwigshafen (DE);
Indre Thiel, Ludwigshafen (DE);
Markus Jegelka, Ludwigshafen (DE);
Jan-Dirk Arndt, Ludwigshafen (DE);
Joaquim Henrique Teles, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 73 days.

This patent is subject to a terminal disclaimer.

(21) Appl. No.: 17/646,766

(22) Filed: Jan. 3, 2022

(65) Prior Publication Data

US 2022/0127241 A1 Apr. 28, 2022

Related U.S. Application Data

(62) Division of application No. 16/634,230, filed as application No. PCT/EP2018/071333 on Aug. 7, 2018, now Pat. No. 11,247,979.

(30) Foreign Application Priority Data

Aug. 17, 2017 (EP) .................... 17186545

(51) Int. Cl.
*C07D 327/04* (2006.01)
*C07D 411/12* (2006.01)

(52) U.S. Cl.
CPC .......... *C07D 327/04* (2013.01); *C07D 411/12* (2013.01)

(58) Field of Classification Search
CPC ................................ C07D 327/04
See application file for complete search history.

(56) References Cited

U.S. PATENT DOCUMENTS

| | | | |
|---|---|---|---|
| 2,820,809 | A | 1/1958 | Frevel et al. |
| 2,828,318 | A | 3/1958 | Reynolds |
| 3,072,676 | A | 1/1963 | Johnson et al. |
| 3,201,416 | A | 8/1965 | Johnson et al. |
| 3,349,100 | A | 10/1967 | Villa |
| 3,517,029 | A | 6/1970 | Johnson |
| 10,889,559 | B2 | 1/2021 | Rudolf et al. |
| 2020/0239633 | A1 | 7/2020 | Rudolf et al. |
| 2020/0299255 | A1 | 9/2020 | Rudolf et al. |
| 2020/0354333 | A1 | 11/2020 | Rudolf et al. |

FOREIGN PATENT DOCUMENTS

| | | |
|---|---|---|
| EP | 2 468 791 | 6/2012 |
| JP | 2005-36084 | 2/2005 |
| JP | 2007-178903 | 7/2007 |
| JP | 2007-320999 | 12/2007 |
| JP | 2010-237645 | 10/2010 |

OTHER PUBLICATIONS

Chemical Abstracts Registry No. 839731-59-8, indexed in the Registry file on STN CAS Online Mar. 1, 2005. (Year: 2005).*
PubChem CID 102253959, National Center for Biotechnology Information. PubChem Compound Summary for CID 102253959, 5-(Allyloxymethyl)-1,3-oxathiolane-2-one. https://pubchem.ncbi.nlm.nih.gov/compound/5-_Allyloxymethyl _-1_3-oxathiolane-2-one. Accessed Jul. 14, 2023, create date Dec. 25, 2015. (Year: 2015).*
V.S. Etlis et al., "Reaction of Chloro Derivatives of Alkene Thiocarbonates with Ammonia and Amines", Doklady Akademii Nauk SSSR = Comptes Rendus De L'academie Des Sciences De L'urss, Akademija Nauk SSSR, vol. 142, No. 4, XP009508894, Jan. 1, 1962, pp. 838-840.
Heinz Fiedler, "*Darstellung von Hydroxy-2-oxo- bzw. -2-thion-1.3-benzoxathiolen*", Chemische Berichte, vol. 95, Issue 7, XP055535091, Jul. 1962, pp. 1771-1785.
International Preliminary Report on Patentability and Written Opinion of the International Searching Authority issued on Feb. 18, 2020 in PCT/EP2018/071333 filed Aug. 7, 2018, 10 pages.
International Search Report issued on Jan. 8, 2019 in PCT/EP2018/071333, 6 pages.
Iskra et al., "*Ring-Opening of 1-CF₃-Substituted Epoxy Ethers with Carboxylic, Thiocarboxylic, and Phosphinic Acids in Basic Medium and in Hexafluoro-2-propanol*", European Journal of Organic Chemistry, vol. 20, 2002, pp. 3402-3410.
N. Kihara et al., "*Preparation of 1,3-Oxathiolane-2-thiones by the Reaction of Oxirane and Carbon Disulfide*", The Journal of Organic Chemistry, vol. 60, Issue 2, Jan. 1, 1995, pp. 473-475.

(Continued)

*Primary Examiner* — Laura L Stockton
(74) *Attorney, Agent, or Firm* — Grüneberg and Myers PLLC

(57) ABSTRACT

A compound of formula IVa

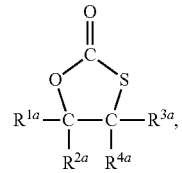

(IVa)

includes two or three $R^{1a}$ to $R^{4a}$ groups which represent hydrogen, and the $R^{1a}$ to $R^{4a}$ groups not being hydrogen represent a group $CH_2$—O—$R^6$, $CH_2$—O—C(=O)—$R^7$, or —$CH_2$—$NR^8R^9$, with $R^6$ to $R^9$ being a linear or branched alkyl group, alkoxy group, polyalkoxy group, or alkenyl group with at maximum 30 carbon atoms.

4 Claims, No Drawings

(56) References Cited

OTHER PUBLICATIONS

M. Luo et al., "*Synthesis of Cyclic Monothiocarbonates Via the Coupling Reaction of Carbonyl Sulfide (COS) with Epoxides*", Catalysis Science & Technology, vol. 6, Aug. 17, 2015, pp. 188-192.

Y. Nishiyama et al., "*A Facile Method for the Synthesis of 1,3-Oxathiolan-2-Ones by Reaction of Oxiranes, Sulfur, and Carbon Monoxide*", Tetrahedron, vol. 62, Issue 24, Jun. 12, 2006, pp. 5803-5807.

PubChem CID 72822, "*1,3-Oxathiolan-2-one*", National Center for Biotechnology Information, PubChem Compound Summary for CID 72822, Mar. 26, 2005.

P.P. Singh et al., "*Studies on 2-Thiazolidinethione, 2,4-Thiazolidinedione and Ethylene Monothiocarbonate Complexes of Sn(IV), Ti(IV) and Fe(II) Halides*", Inorganica Chimica Acta, vol. 18, XP055535116, 1976, pp. 19-23.

Y. Taguchi et al., "*The Reaction of Oxiranes with Carbon Disulfide under High Pressure*", Bulletin of the Chemical Society of Japan, vol. 61, Issue 3, Mar. 1988, pp. 921-925.

Y. Wang et al., "*Cooperative Catalysis with Binary Lewis Acid-Lewis Base System for the Coupling of Carbon Disulfide and Epoxides*", Applied Organometallic Chemistry, vol. 26, Issue 11, Sep. 20, 2012, pp. 614-618.

E. Ziegler et al., "*Synthesen von Heterocyclen, 25. Mitt.: Über Pyrono-cumarine*", Monatshefte für Chemie und verwandte Teile anderer Wissenschaften, vol. 90, Issue 6, XP055535097, Nov. 1959, pp. 866-871.

U.S. Appl. No. 16/639,339, filed Feb. 14, 2020, 2020/0354333, Rudolf et al.

U.S. Appl. No. 16/639,204, filed Feb. 14, 2020, 2020/0239633, Rudolf et al.

U.S. Office Action dated May 31, 2023, in U.S. Appl. No. 16/639,339, 17 pages.

Liu et al., "Potassium Thioacids Mediated Selective Amide and Peptide Constructions Enabled by Visible Light Photoredox Catalysis", ACS Catalysis, vol. 6, 2016, pp. 1732-1736.

Liu et al., Supporting Information for "Potassium Thioacids Mediated Selective Amide and Peptide Constructions Enabled by Visible Light Photoredox Catalysis", ACS Catalysis, vol. 6, 2016, 53 pages.

\* cited by examiner

THIOCARBONATE COMPOUNDS

CROSS-REFERENCE TO RELATED APPLICATIONS

This application is a divisional of U.S. application Ser. No. 16/634,230, filed on Jan. 27, 2020, which was the National Stage entry under § 371 of International Application No. PCT/EP2018/071333, filed on Aug. 7, 2018, and which claims the benefit of priority to European Application No. 17186545.4, filed on Aug. 17, 2017. The content of each of these applications is hereby incorporated by reference in its entirety.

BACKGROUND OF THE INVENTION

Field of the Invention

Object of the present invention is a process for the preparation of a compound with at least one five-membered cyclic monothiocarbonate group wherein
 a) a compound with at least one epoxy group is used as starting material
 b) the compound is reacted with phosgene or an alkyl chloroformate thus giving an adduct and
 c) the adduct is reacted with a compound comprising anionic sulfur thus obtaining the compound with at least one five-membered cyclic monothiocarbonate group.

Description of Related Art

Monothiocarbonates are useful starting materials for the synthesis of chemical compounds. So far, however, monothiocarbonates have not been used in any industrial processes in significant amounts.

Different methods for the synthesis of monothiocarbonates are described in the state of the art.

According to the process disclosed in U.S. Pat. No. 3,349,100 alkylene monothiocarbonates are obtained by reacting an epoxide with carbonylsulfide. The availability of carbonylsulfide is limited. Yields and selectivities of alkylene monothiocarbonates obtained are low. M. Luo, X.-H, Zhang and D. J. Darensbourg, Cat. Sci. Techol. 2015, published on Aug. 17, 2015 describe the use of guanidine as catalysts in the process of U.S. Pat. No. 3,349,100.

A synthesis using phosgene as starting material is known from U.S. Pat. No. 2,828,318. Phosgene is reacted with hydroxymercaptanes. Yields of monothiocarbonates are still low and by products from polymerization are observed.

Object of U.S. Pat. Nos. 3,072,676 and 3,201,416 is a two-step-process for the preparation of ethylene monothiocarbonates. In a first step mercaptoethanol and chlorocarboxylates are reacted to give hydroxyethylthiocarbonate, which is heated in the second step in a presence of metal salt catalyst to the ethylene monothiocarbonate.

According to U.S. Pat. No. 3,517,029 alkylene monothiocarbonates are obtained by reacting mercaptoethanol and a carbonate diester in the presence of a catalytically active salt of thorium.

Yoichi Taguchi et al., Bull. Chem. Soc. Jpn., 1988, 61, 921-921 disclose the formation of monothiocarbonate by reacting carbon disulfide and 2,2 dimethyloxirane in the presence of trimethylamine.

Yutaka Nishiyama et al., Tetrahedron, 2006, 62, 5803-5807 disclose the formation of monothiocarbonate using epoxide, sulfur and carbon monoxide as reactants in the presence of sodium hydride.

M. Luo, X.-H. Zhang and D. J. Darensbourg, Catalysis Science & Technology, 2015, article accepted on Aug. 13, 2015 (DOI: 10.1039/c5cy00977d) disclose some specific cyclic monothiocarbonates obtained via coupling reaction of carbonyl sulfides with epoxides.

Yi-Ming Wang, Bo Li, Hui Wang, Zhi-Chao Zhang and Xiao-Bing Lu, Appl. Organometal. Chem. 2012, 26, 614-618 also disclose some specific cyclic monothiocarbonates obtained via coupling reaction of carbonyl sulfides with epoxides.

The object of EP-A 2468791 are epoxy compositions that comprise compounds with five membered cyclic ring system comprising oxygen and sulfur. The compounds disclosed in EP-A 2468791 and in J. Org. Chem. 1995, 60, 473 to 475 cited in EP-A 2468791, are compounds with five membered cyclic ring system comprising at least 2 sulfur atoms. Compounds with one sulfur atom are not mentioned.

None of the processes described above has gained industrial importance due to their deficiencies. Many of these processes involve the use of starting materials of low availability, high costs or problematic properties. Furthermore, yields and selectivities, in particular selectivity of structural isomers, obtained are not yet satisfying for production on industrial scale. As a consequence, the availability of thiocarbonates in commercial quantities is low even though thiocarbonates are of high interest as intermediates in chemical synthesis.

SUMMARY OF THE INVENTION

Hence, it was an object of this invention to provide a process to produce thiocarbonates which is useful for industrial scale production. The process should not involve expensive starting materials or starting materials of low availability. The process should be easy to perform, should be as economic as possible and give thiocarbonates in high yield and selectivity.

Accordingly, the above process for the preparation of a compound with at least one five-membered cyclic monothiocarbonate group has been found.

A five-membered cyclic monothiocarhonate group is a ring system with 5 members, three of them are from the monothiocarbonate —O—C(=O)—S— and the further two members are carbon atoms closing the five-membered cycle.

DETAILED DESCRIPTION OF THE INVENTION

To the process
a) Epoxy Compounds

Starting compound for the process is a compound with at least one epoxy group.

In a preferred embodiment of the invention the compound with at least one epoxy group is
 i) a glycidyl compound
 ii) a non-glycidyl compound A glycidyl compound is a compound with at least a glycidyl group or a derivative, thereof. Examples for i) are epichlorohydrin or derivatives thereof wherein the chloride of epichlorohydrin is replaced by a hydroxy group (glycidol) ether group (glycidyl ether), ester group (glycidyl ester) or amino group (glycidyl amine) or an imide group (glycidyl imide).

Further examples for i) are any compounds obtained by reacting
compounds with at least one glycidyl group and at least one functional group such as chloride or a hydroxy group, for example epichlorohydrin or glycidol with compounds that are reactive with such functional group In a particularly preferred embodiment, compounds i) are selected from epichlorohydrin, a glycidyl ether, a glycidyl ester, a glycidyl amine or glycidyl imide or a compound with at least one glycidyl group or at least one glycidyl ether group or at least one glycidyl ester group or at least one glycidyl amino group or at least one glycidyl imide group.

The compound may be a compound with only one epoxy group, such epoxy-compounds are usually low molecular weight compounds with a molecular weight below 5000 g/mol, in particular below 1000 g/mol, more specifically below 500 g/mol. A compound with only one epoxy group could be, for example, epichlorhydrin or a glycidylether or a glycidylester or propylenoxide.

The compound may comprise more than one epoxy group. Such compounds are, for example, fatty acids, fatty acid esters or fatty alcohols with at least two unsaturated groups that have been transferred into epoxy groups. Further compounds with at least two epoxy groups are poly glycidylethers, in particular diglycidyl ethers, for example bisphenol diglycidyl ethers. Compounds which are polymers or oligomers may comprise a high number of epoxy groups. Such compounds are, for example, obtainable by polymerization or copolymerization of monomers with epoxy groups or by converting functional groups of polymers into epoxy groups. Compounds with more than one epoxy group may comprise, for example, up to 1000, in particular up to 500, preferably up to 100 epoxy groups. Further polymers with epoxy groups are, for example, novolacs that have been epoxidized by reacting them with epichlorhydrin to novolac-polyglycidylether.

Examples for ii) are compounds with one, two or three epoxy groups obtained by oxidizing olefins, di-olefins or tri-olefins, or cyclic olefins, unsaturated fatty acids, fatty acid esters or fatty alcohols.

In a preferred embodiment, the compound with at least one epoxy group is a compound with 1 to 100, more preferably 1 to 10 and in a most preferred embodiment with 1 to 3, notably 1 or 2 epoxy groups.

b) First Process Step, Formation of Adduct

In the first process step the compound with at least one epoxy group is reacted with phosgene or an alkyl chloroformate thus giving an adduct. Preferably, it is reacted with phosgene. The word phosgene shall include any phosgene substitutes; phosgene substitutes are compounds that set free phosgene. A phosgene substitute is, for example, triphosgene.

Below the reaction of step b) is shown exemplarily for a specific epoxy compound substituted by R and phosgene as reactant.

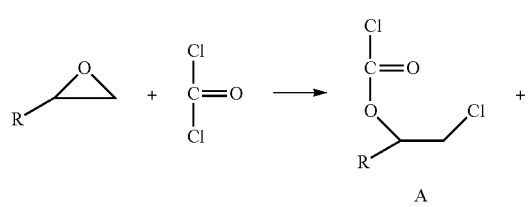

A

-continued

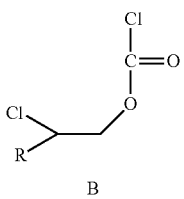

B

Two structural isomers of β-chloroalkyl chloroformate A and B are obtained. It is an advantage of the present invention that the product has a high selectivity regarding the structural isomers. In particular, at least 80%, preferably at least 90% usually at least 95% of the adduct correspond to isomer A.

The compound with at least one epoxy group may be reacted with phosgene or an alkyl chloroformate in any stochiometric ratio. Preferably, a very high excess of the compound with at least one epoxy group is avoided, as such a high excess would result in high amounts of unreacted starting compounds which would have to be removed during work-up of the obtained product composition.

Preferably, the phosgene, respectively chloroformate, are used in an amount of 0.1 to 5 mol, in particular of 0.5 to 2 mol per mol of each epoxy group of the compound with at least one epoxy group. In a particularly preferred embodiment the phosgene, respectively chloroformate, are used in excess.

With at least equimolar amounts of phosgene, respectively chloroformate, epoxy groups that remain unreacted can be avoided. Hence, in a preferred embodiment the phosgene, respectively chloroformate, are used in an amount of 0.9 to 5 mol, more preferably of 1 to 2 mol, in particular 1 to 1.5 mol per mol of each epoxy group of the compound with at least one epoxy group.

In case that products are desired that still comprise epoxy groups, a less than equimolar amount of phosgene, respectively chloroformate, is preferably used per mol of each epoxy group. Alternatively, the reaction may be stopped when the desired amount of epoxy groups is still unreacted.

The obtained product may still comprise epoxy groups.

A specific product of interest could be, for example, a compound comprising one epoxy group and one five-membered cyclic monothiocarbonate group. If such a compound is desired, 0.5 mol of phosgene, respectively chloroformate, may, for example, be used per mol of each epoxy group. As an example of a compound comprising one epoxy group and one five-membered cyclic monothiocarbonate group see the reaction scheme below, starting form a di-epoxide and resulting in a compound with one monothiocarbonate and with still one epoxide group.

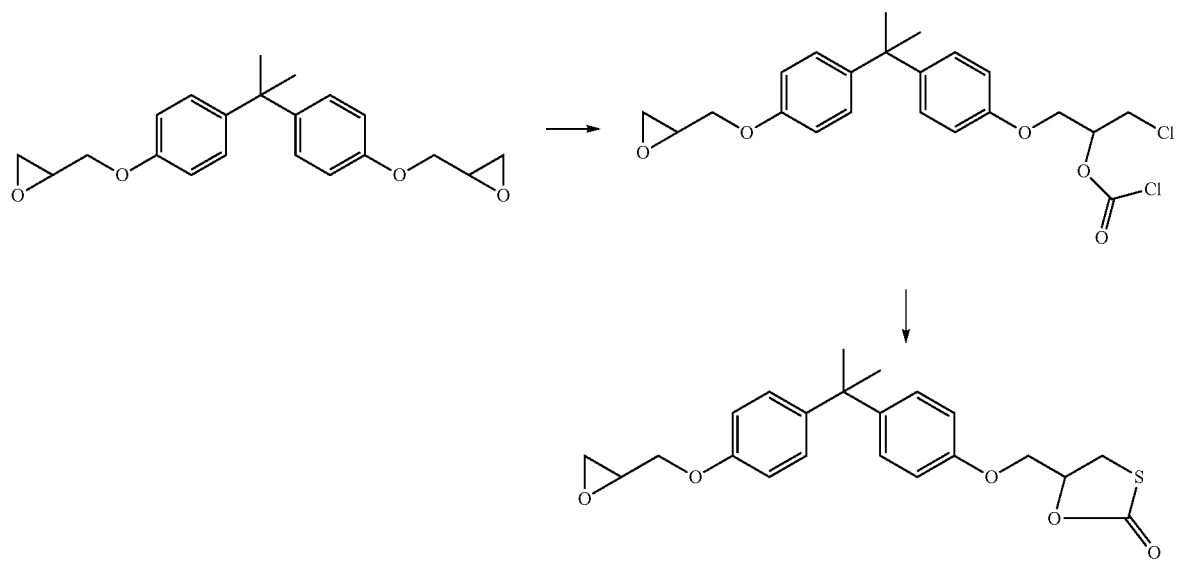

The phosgene and the chloroformate are preferably a compound of formula II

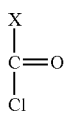

wherein X is Cl in case of phosgene or a group O—R5 with R5 representing a C1- to C4 alkyl group in case of chloroformate.

In a preferred embodiment the compound with at least one epoxy group is reacted with phosgene.

Preferably, the reaction is performed in presence of a catalyst. Suitable catalysts are salts with a quaternary ammonium cation such as tetraalkylammonium halogenides, in particular chlorides, for example tetrabutylammoniumchloride, tetrahexylammoniumchloride, benzyltributylammonium chloride or trioctylmethylammonium chloride.

Further suitable catalysts are, for example, hexa-alkylguanidinium halogenides, in particular chlorides, quarternary phosphonium halogenides, in particular chlorides, pyridine or other compounds with a ring system comprising nitrogen such as imidazole or alkylated imidazole.

Preferred catalysts are salts with a quaternary ammonium cation, in particular salts of tetra alkyl ammonium, for example tetra (n-butyl) ammonium chloride.

Preferably, the catalyst is used in an amount of 0.001 to 0.1 mol, in particular in an amount of 0.005 to 0.05 mol per mol of epoxy group.

The phosgene or alkyl chloroformate is preferably added to the compound with at least one epoxy group. As the reaction is exothermic, addition of phosgene or alkyl chloroformate is preferably made slowly so that the temperature of the reaction mixture is kept at the desired value. Preferably, the reaction mixture is cooled during the addition.

Preferably, the temperature of the reaction mixture is kept at −40 to 60° C., notably at 5 to 50° C.

Low molecular compounds with at least one epoxy group are usually liquid; hence, an additional solvent is not required. Preferably, a solvent is used in case of compounds with at least one epoxy group that are solid at 21° C. Suitable solvents are, in particular aprotic solvents. Suitable solvents are, for example, hydrocarbons, including aromatic hydrocarbons and chlorinated hydrocarbon, such as for example toluene, chloro-benzene or dichloro-benzene.

A preferred solvent for a solid compound with epoxy groups is an additional liquid compound with epoxy groups. The liquid compound together with the solid compound undergo the reaction as described in process steps b) and c). The monothiocarbonate obtained from the liquid compound would usually be liquid as well and, therefore, would serve also as solvent for the most probably solid monothiocarbonate obtained from the solid compound with at least one epoxy group.

When the reaction is completed, unreacted phosgene or chloroformate may be removed from the mixture by distillation. No further work up is necessary. The product mixture obtained comprises a compound with at least one β-chloro alkylchlorformate group. The next process step may follow immediately.

c) Second Process Step, Formation of the Monothiocarbonate Groups

Below the reaction under b) is exemplarily shown for a specific epoxy compound substituted by R and phosgene as reactant. Starting with the β-chloro alkylchlorformates formed above, the second process step c) can be exemplarily shown for Na₂S as reactant as follows:

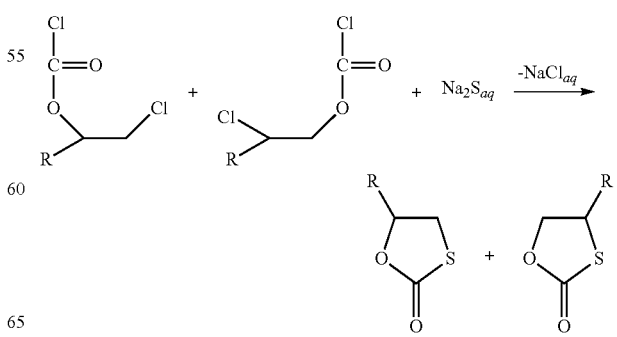

In this step the ratio of structural isomers A and B obtained in the first step and hence the selectivity is preserved.

Preferably, the product mixture obtained under b) is used under process step c) without any further work-up.

A solvent may be added in step c). Suitable solvents are, in particular, aprotic solvents. Suitable solvents are, for example, hydrocarbons, including aromatic hydrocarbons and chlorinated hydrocarbon or hydrophilic aprotic solvents, for example ethers such as tetrahydrofuran, dioxane, polyether such as glyms, acetonitrile or dimethylsulfoxid.

The product mixture from step b) is reacted with a compound comprising anionic sulfur. The compound comprising anionic sulfur is preferably a salt.

The anionic sulfur is preferably $S^{2-}$, a polysulfide of formula $(S_p)^{2-}$ with p being an integral number from 2 to 200, preferably from 2 to 10 or $HS^{1-}$.

The cation of the salt may be any organic or inorganic cation. Preferably, it is an inorganic cation, in particular a metal. Usual metal cations are, for example, cations of alkali or earth alkali metals, such as sodium or potassium.

Preferred salts are $Na_2S$, $K_2S$, NaSH or KSH or any hydrates thereof.

The salt may be used in combination with a basic compound, in particular a metal hydroxide, such as, in particular, NaOH or KOH. Such an additional basic compound is preferably used in case of salts with $SH^-$ as anion.

The anionic sulfur may also be generated in situ, starting from sulfur or a compound comprising sulfur in non-ionic form. For example $H_2S$ may be used as source for anionic sulfur. In presence of a basic compound, for example NaOH (see above), anionic sulfur is obtained from $H_2S$ in situ.

The salt with anionic sulfur, respectively the compound from which anionic sulfur is generated in situ (together referred herein as the sulfur compound), is preferably added to the product mixture obtained in b). The sulfur compound may be added as such or, for example, as solution in a suitable solvent, such as water. In a preferred embodiment of the invention, the sulfur compound is dissolved in a solvent, in particular water, and the solution is added.

If the sulfur compound is added as solution in water, a two-phase system comprising an organic and an aqueous phase is obtained and the reaction occurs in such two-phase system. If a one phase system is desired instead, a suitable solvent may be added which acts as intermediary to combine the aqueous and organic phase to one phase again. A suitable solvent may be a hydrophilic aprotic solvent, for example a hydrophilic aprotic solvent listed above.

As the reaction is exothermic as well, addition of the salt, respectively the solution of the salt, is preferably made slowly so that the temperature of the reaction mixture is kept at the desired value. Preferably, the reaction mixture is cooled during the addition.

The reactants may be added or combined in any order. For example, the sulfur compound may be added to the β-chloro alkylchlorformate as described above. Alternatively, the β-chloro alkylchlorformate may be added to the compound comprising anionic sulfur.

Preferably, the temperature of the reaction mixture is kept at −40 to 60° C., notably at −10 to 50° C.

Preferably, the salt is added in an amount of 0.5 to 2.0 mol per mol of each β-chloro alkylchlorformate group of the compound with at least one β-chloro alkylchlorformate group.

Preferably, the salt is added in an amount of 1.0 to 2.0 mol per mol of each β-chloro alkylchlorformate group of the compound with at least one β-chloro alkylchlorformate group.

In a most preferred embodiment, the salt is added in an amount of 1.0 to 1.3 mol per mol of each β-chloro alkylchlorformate group of the compound with at least one β-chloro alkylchlorformate group, as no significant excess of the salt is required to get a quick and complete reaction of all β-chloro alkylchlorformate groups.

By reaction with the salt the β-chloro alkylchlorformate groups are transferred into five-membered cyclic monothiocarbonate groups. The five-membered ring system is formed from three carbon atoms, one oxygen and one sulfur with a further oxygen double bonded to the carbon atom which is located between the oxygen and the sulfur of the ring system.

If desired, the second process step may be performed in the presence of a catalyst. Such a catalyst is, for example, a phase transfer catalyst such as ammonium salts, heterocyclic ammonium salts and phosphonium salts.

The final product obtained under c) may be worked up by extracting with a hydrophilic solvent, preferably water. In case that the above salt of anionic sulfur has been used in form of an aqueous solution nor further water may be required. The organic and aqueous phase are separated. The organic phase may be washed with water which has preferably a pH of 4 to 10, in particular a pH of at least 7. The organic phase comprises the compound with at least one monothiocarbonate group. The aqueous phase comprises unreacted sulfide/hydrogesulfide salt and/or NaCl and at least partially any catalyst added.

Any solvent may be removed from the organic phase by distillation. The obtained compound with at least one monothiocarbonate group may be further purified by distillation or may be used without further purification.

Hence, compounds with at least one five-membered cyclic monothiocarbonate group are obtained by the above process.

To the preparation of a compound with one five-membered cyclic monothiocarbonate group A preferred process for the preparation of a compound with one five-membered cyclic monothiocarbonate group comprises a) an epoxy compound of formula Ia

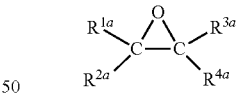

with $R^{1a}$ to $R^{4a}$ independently from each other representing hydrogen or an organic group with up to 50 carbon atoms whereby, alternatively, $R^{2a}$, $R^{4a}$ and the two carbon atoms of the epoxy group may also together form a five to ten membered carbon ring as starting material, b) reacting the epoxy compound with a compound of formula II

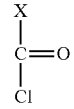

wherein X is Cl (phosgene) or a group O—R$^5$ with R$^5$ representing a C1- to C4 alkyl group (chloroformate) to give an adduct of formula IIIa

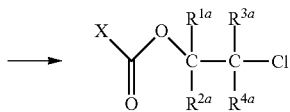

wherein R$^{1a}$ to R$^{4a}$ have the meaning above and
c) reacting the adduct of formula IIIa with a compound comprising anionic sulfur to the monothiocarbonate of formula IVa

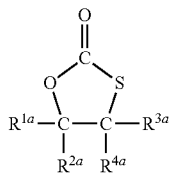

wherein R$^{1a}$ to R$^{4a}$ have the meaning above.

In case that any of R$^{1a}$ to R$^{4a}$ represent an organic group, such organic group is preferably an organic group with up to 30 carbon atoms. In a further preferred embodiment R$^{2a}$ and R$^{4a}$ do not form a five to ten membered carbon ring together with the two carbon atoms of the epoxy group.

In case that any of R$^{1a}$ to R$^{4a}$ represent an organic group, such organic group may comprise other elements than carbon and hydrogen. In particular, it may comprise oxygen, nitrogen, sulfur and chloride. In a preferred embodiment the organic group may comprise oxygen or chloride. R$^{1a}$ to R$^{4a}$ may comprise oxygen for example in form of ether, hydroxy, aldehyde, keto or carboxy groups.

Preferably, at least one of R$^{1a}$ to R$^{4a}$ in formula Ia and accordingly in formulas IIIa and IVa is not hydrogen.

More preferably, two and or three of R$^{1a}$ to R$^{4a}$ in formula Ia and accordingly in formulas IIIa and IVa represent hydrogen and the remaining groups R$^{1a}$ to R$^{4a}$ represent an organic group.

Most preferably, three of R$^{1a}$ to R$^{4a}$ in formula Ia and accordingly in formulas IIIa and IVa represent hydrogen and the remaining group of R$^{1a}$ to R$^{4a}$ represents an organic group.

In a preferred embodiment R$^{1a}$ or R$^{2a}$ is the remaining group representing an organic group.

The remaining groups or the remaining group of R$^{1a}$ to R$^{4a}$ preferably represent a hydrocarbon group with up to 30 carbon atoms which may comprise oxygen, nitrogen or chloride, in particular oxygen.

In a preferred embodiment, the remaining groups or the remaining group represent a group —CH$_2$—O—R$^6$ or —CH$_2$—O—C(═O)—R$^7$ or —CH$_2$—NR$^8$R$^9$ with R$^6$ to R$^9$ being an organic group with up to 30 carbon atoms, preferably up to 20 carbon atoms. In particular, R$^6$ to R$^9$ represent an aliphatic, cycloaliphatic or aromatic group, which may comprise oxygen, for example in form of ether groups. In a preferred embodiment, R$^6$ to R$^3$ represent a linear or branched alkyl group, alkoxy group, polyalkoxy group or alkenyl group. In a most preferred embodiment, R$^6$ to R$^9$ represent a linear or branched alkyl group or alkenyl group.

In a most preferred embodiment, the remaining groups or the remaining group represent a group —CH$_2$—O—R$^6$ or —CH$_2$—O—C(═O)—R$^7$.

As preferred compounds with one five-membered cyclic monothiocarbonate group obtained by the process may be mentioned:

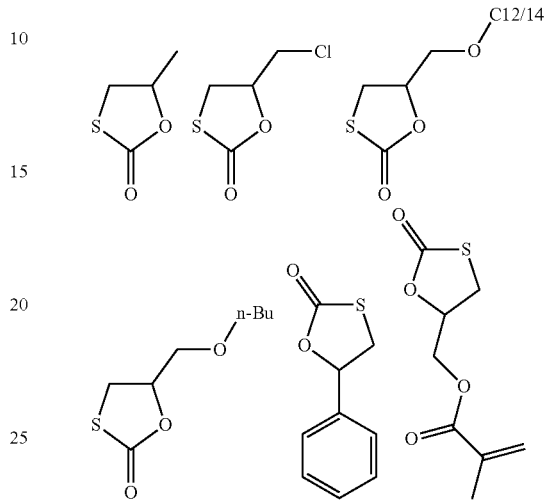

In addition, the monothiocarbonate compounds obtained from epoxides selected from ethylene oxide, propylene oxide, butylene oxide, isobutylene oxide, methyl-3,4-epoxycyclohexanecarboxylate, 3,4-epoxycyclohexylmethyl 3,4-epoxycyclohexanecarboxylate, are mentioned.

All disclosure in this patent application relating to process steps b) and c) apply to the above preparation of a compound with one five-membered cyclic monothiocarbonate group.

Compounds of formula IVa,

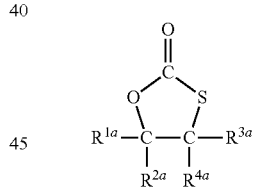

wherein two or three of R$^{1a}$ to R$^{4a}$ represent hydrogen and the groups R$^{1a}$ to R$^{4a}$ not being hydrogen represent a group CH$_2$—O—R$^6$ or —CH$_2$—O—C(═O)—R$^7$ or —CH$_2$—NR$^8$R$^9$ with R$^6$ to R$^9$ being a linear or branched alkyl group, alkoxy group, polyalkoxy group or alkenyl group with at maximum 30 carbon atoms have not been produced by processes of the prior art and are now accessible by the new process described hereunder.

Processes for the production of monothiocarbonates known from the prior art usually give mixtures of structural isomers. With the process of this invention the content of structural isomers is significantly reduced. Mixtures of isomers A and B with very low amount of B are obtainable, see above.

In a preferred embodiment, the compound of formula IVa is a mixture of two structural isomeric compounds A and B of formula IVa wherein isomer A is a compound with R$^{1a}$ being a group CH$_2$—O—R$^6$ or CH$_2$—O—C(═O)—R$^7$ or —CH$_2$—NR$^8$R$^9$ and R$^{2a}$, R$^{3a}$ and R$^{4a}$ being hydrogen and isomer B is a compound with $R^{3a}$ being a group $CH_2$—O—$R^6$ or $CH_2$—O—C(=O)—$R^7$ or —$CH_2$—$NR^8R^9$ and $R^{1a}$, $R^{2a}$ and $R^{4a}$ being hydrogen and wherein the mixture consists of 90 to 99.9% by weight of A and 0.1 to 10% by weight of B, based on the sum of A and B. Preferably, the mixture consists of 95 to 99.9%, respectively 95 to 99.5% by weight of A and 0.1 to 5 respectively 0.5 to 5% by weight of B.

A particularly preferred compound of formula IVa is a compound wherein $R^{2a}$ to $R^{4a}$ in formula IVa represent hydrogen and $R^{1a}$ is a group —$CH_2$—O—$R^6$ or a group —$CH_2$—O—C(=O)—$R^7$ or a group —$CH_2$—$NR^8R^9$ with $R^6$ to $R^9$ being an C1 to C14 alkyl group, preferably a C4 to C14 alkyl group.

To the preparation of a compound with more than one five-membered cyclic monothiocarbonate group A preferred process relating to the preparation of a compound with more than one five-membered cyclic monothiocarbonate group comprises a) an epoxy compound of formula Ib

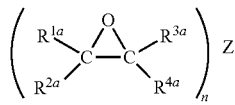

with $R^{1b}$ to $R^{4b}$ independently from each other representing hydrogen or an organic group with up to 50 carbon atoms whereby, alternatively, $R^{2b}$, $R^{4b}$ and the two carbon atoms of the epoxy group may also together form a five to ten membered carbon ring and one of the groups $R^{1b}$ to $R^{4b}$ is a linking group to Z, n representing an integral number of at least 2 and Z representing a n-valent organic group, as starting material, b) reacting the compound with a compound of formula II

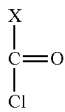

wherein X is Cl (phosgene) or a group O—$R^5$ with $R^5$ representing a C1- to C4 alkyl group (chloroformate) to give an adduct of formula IIIb

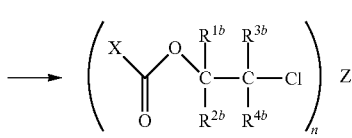

wherein $R^{1b}$ to $R^{4b}$, Z and n have the meaning above and c) reacting the adduct of formula IIIb with a compound comprising anionic sulfur to a compound of formula IVb comprising at least two monothiocarbonate groups

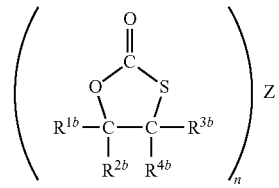

wherein $R^{1b}$ to $R^{4b}$, Z and n have the meaning above.

In case that any of $R^{1b}$ to $R^{4b}$ represent an organic group, such organic group is preferably an organic group with up to 30 carbon atoms. In a further preferred embodiment $R^{2b}$ and $R^{4b}$ do not form a five to ten membered carbon ring together with the two carbon atoms of the epoxy group.

In case that any of $R^{1b}$ to $R^{4b}$ represent an organic group, such organic group may comprise other elements than carbon and hydrogen. In particular, it may comprise oxygen, nitrogen, sulfur and chloride. In a preferred embodiment the organic group may comprise oxygen or chloride. $R^{1b}$ to $R^{4b}$ may comprise oxygen for example in form of ether, hydroxy, aldehyde, keto or carboxy groups.

One of the groups $R^{1b}$ to $R^{4b}$ is the linking group to Z.

Preferably, the linking group is simply a bond or a group $CH_2$—O— or $CH_2$—O—C(=O)— or $CH_2$—$NR^{20}$— with $R^{20}$ being an aliphatic group, in particular an alkyl group with at maximum 20 carbon atoms, or a group C(=O)—O— or a group $R^{21}$—C(=O)—O— wherein $R^{21}$ is an organic group, preferably a hydrocarbon group with up to 20 carbon atoms.

More preferably, the linking group is simply a bond or a group $CH_2$—O— or a group $CH_2$—O—C(=O)—.

In a most preferred embodiment, the linking group is a group $CH_2$—O—.

Preferably, two or three of the groups $R^{1b}$ to $R^{4b}$ in formula Ib and accordingly in formulas IIIb and IVb are hydrogen.

In a most preferred embodiment three of the groups $R^{1b}$ to $R^{4b}$ represent hydrogen and the remaining group of $R^{1b}$ to $R^{4b}$ is the linking group to Z.

In a most preferred embodiment groups $R^{1b}$ or $R^{2b}$ is the linking group to Z.

With the linking groups $CH_2$—O— or $CH_2$—O—C(=O)— or $CH_2$—$NR^{20}$— and with the preferred embodiment that three of $R^{1b}$ to $R^{4b}$ are hydrogen, the group in the bracket of formula Ib becomes a glycidylether group of formula

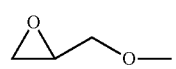

or a glycidylester group of formula

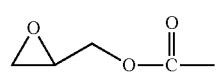

or a glycidylamino group of formula

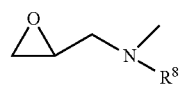

In a most preferred embodiment the group in the bracket of formula Ib is the above glycidylether group or glycidylester group.

In the embodiment that $R^{2b}$ and $R^{4b}$ do form a five to ten membered carbon ring together with the two carbon atoms of the epoxy group, the linking groups mentioned above may alternatively be bonded to the carbon atoms of the ring system.

n represents an integral number of at least 2, For example, n may be an integral number from 2 to 1000, in particular from 2 to 100 respectively 2 to 10.

In a preferred embodiment n is an integral number from 2 to 5, in particular n is 2 or 3.

In a most preferred embodiment n is 2.

Z represents a n-valent organic group. In case of high number of n, such as, for example, 10 to 1000, Z may be a polymeric backbone of a polymer obtained, for example, by polymerization copolymerization, such as radical polymerization of ethylenically unsaturated momomers, polycondensation or polyaddition. For example, polymers like polyesters or polyamides are obtained via polycondensation under elimination of water or alcohol and, for example, polyurethanes or polyureas are obtained via polyaddition.

Compounds of formula Ib are, for example, polymers with epoxy groups obtained by radical polymerization or copolymerization of ethylenically unsaturated momomers such as glycidyl (meth) acrylate or novolac-polyglycidylether obtained by reacting novolac with, for example, epichlorohydrin or methyl-3,4-epoxycyclohexanecarboxylate.

In a preferred embodiment Z is a n-valent organic group with up to 50 carbon atoms, in particular up to 30 carbon atoms, and which may comprise other elements than carbon and hydrogen and n is an integral number from 2 to 5, notably 2 or 3, most preferred 2.

In a particularly preferred embodiment Z is a n-valent organic group with up to 50 carbon atoms, in particular up to 30 carbon atoms, and which comprises carbon, hydrogen and optionally oxygen, only and no further elements and n is an integral number from 2 to 5, notably 2 or 3, most preferred 2.

In a preferred embodiment Z is a polyalkoxylene group of formula G1

wherein V represents a C2- to C20 alkylen group and m is an integral number of at least 1. Preferably, the C2-C20 alkylen group is a C2- to C4 alkylen group, in particular ethylene or propylene. m may, for example be an integral number from 1 to 100, in particular from 1 to 50. The terminal alkylene groups V are bonded to the linking group, which is one of the groups $R^{1b}$ to $R^{4b}$, see above.

In a further preferred embodiment Z is a group of formula G2

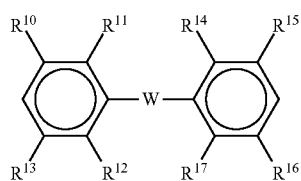

wherein W is a bi-valent organic group with at maximum 10 carbon atoms and n is 2 and $R^{10}$ to $R^{17}$ independently from each other represent H or a C1- to C4 alkyl group. Preferably, at least six of $R^{10}$ to $R^{17}$ are hydrogen. In a most preferred embodiment all of $R^{10}$ to $R^{17}$ are hydrogen.

The two hydrogen atoms in the para position to W are replaced by the bond to the linking group, which is one of the groups $R^{1b}$ to $R^{4b}$, see above.

Groups W are, for example:

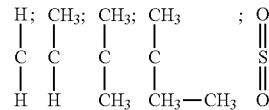

Preferably, W is an organic group that consists of carbon and hydrogen, only.

Most preferred W is

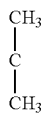

which corresponds to the structure of bisphenol A.

In a further preferred embodiment Z is a group G3, wherein G3 represents an alkylene group, notably a C2 to C8 alkylene group; preferred examples of such an alkylene group are ethylene ($CH_2$—$CH_2$), n-propylen ($CH_2$—$CH_2$—$CH_2$) and notably n-butylene ($CH_2$—$CH_2$—$CH_2$—$CH_2$).

Examples for preferred compounds with more than one five-membered cyclic monothiocarbonate group compounds are in particular those which are obtained by transferring all epoxy groups of the following epoxy compounds into five-membered cyclic monothiocarbonate groups:

Non-Glycidyl Epoxides:
  1,2:5,6-diepoxyhexahydro-4,7-methanoindan, bis (3,4-epoxycyclohexylmethyl) adipate, 1,4-cyclohexanedimethanol bis(3,4-epoxycyclohexanecarboxylate, 1-methyl-4-(2-methyloxiranyl)-7-oxabicyclo[4.1.0]heptane, 4-vinylcyclohexene dioxide, 1,2,5,6-diepoxycyclooctane, 1,2,7,8-diepoxyoctane, dicyclopentadiene dioxide, epoxidized plant oils or epoxidized fatty esters such as soy bean oil derived compounds or reaction products of polyols and methyl-3,4-epoxycyclohexanecarboxylate.

Glycidylether:
  bisphenol A diglycidylether (BADGE), hydrogenated BADGE, glycidylether of other di-, tri, tetra- and polyols such as butandiol-diglycidylether, trimethylolpropan-triglycidyiether, pentaerythritol tetraglycidyl ether, Sorbitol polyglycidylether, isosorbide diglycidylether, 2-methyl-2-phenyl-1,3-propandioldiglycidylether, allyl glycidylether, 4-vinyl-1-cyclohexene 1,2-epoxide. This includes also oligomeric/polymeric glycidylether such as e.g. polypropylenglycoldiglycidylether, polyglycerolpolyglycidylether, novolac-glycidylether, oligomers or polymers obtained by reacting bispenol A with an excess of epichlorhydrin.

Glycidylester:
  tetrahydrophthalic acid diglycidyl ester, diglycidyl 1,2-cyclohexanedicarboxylale, versatic acid glycidylester, diglycidylorthophthalate, glycidylmethacrylate.

Glycidyl Amine:
  N,N-diglycidyl-4-glycidyloxyaniline, tetraglycidylmethylenedianiline Glycidylimide:
  triglycidyl isocyanurate All disclosure in this patent application relating to process steps b) and c) apply to the above preparation of a compound with more than one five-membered cyclic monothiocarbonate group.

Compounds of formula IVb

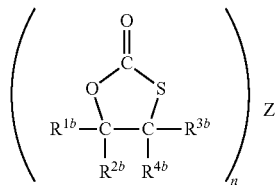

with $R^{1b}$ to $R^{4b}$ independently from each other representing hydrogen or an organic group with up to 50 carbon atoms whereby, alternatively, $R^{2b}$, $R^{4b}$ and the two carbon atoms of the epoxy group may also together form a five to ten membered carbon ring and one of the groups $R^{1b}$ to $R^{4b}$ is a linking group to Z, n representing an integral number of at least 2 and Z representing a n-valent organic group.

These compounds have not been produced by processes of the prior art and are now accessible by the new process described hereunder.

This applies in particular to compounds IVb wherein n is 2 and Z is a polyalkoxylene group of formula G1

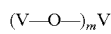

wherein V represents a C2- to C20 alkylen group and in is an integral number of at least 1 and wherein each of the two terminal alkylene groups V is bonded to the linking group, which is one of the groups $R^{1b}$ to $R^{4b}$.

This applies furthermore in particular to compounds of formula IVb wherein n is 2 and Z is a group of formula G2

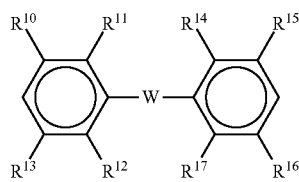

wherein W is a bi-valent organic group with at maximum 10 carbon atoms and $R^{10}$ to $R^{17}$ independently from each other represent H or a C1- to C4 alkyl group and wherein the two hydrogen atoms in the para position to W are replaced by the bond to the linking group, which is one of the groups $R^{1b}$ to $R^{4b}$.

And this applies furthermore to compounds of formula IVb wherein n is 2 and Z is a group G3, which is an alkylene group, see above.

To the preparation of a compound with at least one five-membered cyclic monothiocarbonate group and at least one epoxy group.

A preferred process for the preparation of a compound with at least one five-membered cyclic monothiocarbonate group and at least one epoxy group is a process which starts with an epoxy compound of formula Ib. However, the compound of formula Ib is reacted with less than equimolar amounts of compound of formula II thus transferring not all epoxy groups into the group shown in the bracket of formula IIIb. As product of the first step a compound of formula IIIc is obtained:

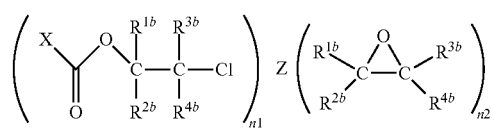

In the second step, the product of the first step is transferred into the final compound of formula IVc:

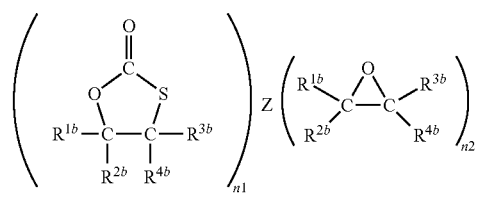

The numbers $n_1$ and $n_2$ are integral numbers and the sum of $n_1$ and $n_2$ gives n as defined above.

All disclosure in this patent application relating to process steps b) and c) and to the preparation of compounds of formula IVb apply to the preparation of compounds of formula IVc, if not explicitly said otherwise in this application.

All definitions of Z and $R^{1b}$ to $R^{4b}$ in formulas Ib to IVb relate to the preparation of compounds IVc and to formulas IIIc and IVc as well.

In a preferred embodiment, the compound of formula IVc is a compound with both $n_1$ and $n_2$ being 1 and the sum being 2.

Preferred compounds with at least one five-membered cyclic monothiocarbonate group and at least one epoxy group are compounds wherein Z is a group G1 or G2 (see above) and both $n_1$ and $n_2$ are 1, the sum being 2.

A specifically preferred example is the following compound:

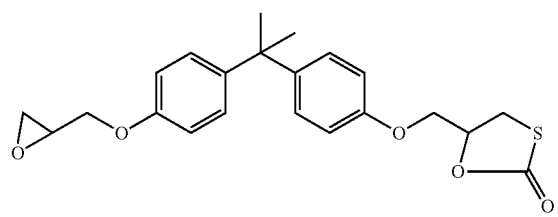 [SMILES: CC(C)(c1ccc(OCC2CO2)cc1)c1ccc(OCC2CSC(=O)O2)cc1]

Finally, it is stated that the preferred compounds with at least one monothiocarbonate group are compounds of formula IVa), IVb), IVc) and compounds which are not covered by formulas IVa), IVb) and IVc) and comprise at least two monothiocarbonate groups that are obtained by oxidization of compounds with at least two ethylenically unsaturated groups, such as olefins, unsaturated fatty acids, unsaturated fatty acid ester or fatty alcohols with at least two ethylenically unsaturated groups.

The more preferred compounds with at least one monothiocarbonate group are compounds of formula IVa), IVb) and compounds which are not covered by formulas IVa), IVb) and IVc) and comprise at least two monothiocarbonate groups that are obtained by oxidization of compounds with at least two ethylenically unsaturated groups, such as olefins, unsaturated fatty acids, unsaturated fatty acid ester or fatty alcohols with at least two ethylenically unsaturated groups.

The most preferred compounds with at least one monothiocarbonate group are compounds of formula IVa) and IVb).

The present invention provides for a very economic and effective process for the production of compounds with at least one five-membered cyclic monothiocarbonate group. The process is suitable for industrial scale production. The process does not involve expensive starting materials or starting materials of low availability. The process gives compounds with at least one five-membered cyclic monothiocarbonate group in high yield and selectivity.

Examples 1 to 6, First Part: Synthesis of β-chloro alkylchlorformates

Epoxide was charged to a reactor and kept at −30° C. The molar amount of epoxide is listed in Table 1. 0.01 mol of tetra(n-butyl ammonium chloride were added per 1 mol of epoxide. Thereafter phosgene is added slowly as the reaction is exothermic. When adding the phosgene the temperature was kept via cooling at the temperature listed in the Table. The time of metering phosgene is listed in the Table. The total amount of phosgene was 1.1 mol per 1 mol of epoxide.

When the addition of phosgene was completed the reaction mixture was further stirred for about (2 hours). Unreacted phosgene was removed by nitrogen stripping. No further work-up was necessary. The obtained β-chloro alkylchlorformates could be used directly in the next step which is the formation of the thiocarbonates.

The epoxide, the obtained β-chloro alkylchlorformates and further details of the reaction are listed in Table 1.

The β-chloro alkylchlorformates are obtained in form of two different structural isomers (stereoisomers) a and b

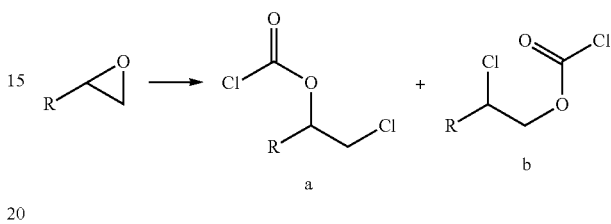

The selectivities regarding a and b are listed in the Table 1 as well. The total yield listed in Table 1 is based on the epoxide used as starting material.

TABLE 1

| | | β-chloro alkylchlorformates | | | |
|---|---|---|---|---|---|
| example | epoxide | β-chloro alkylchlorformates | T [° C.] | selectivity a:b | total yield (a + b) [%] |
| 1 |  (1.6 mol) | 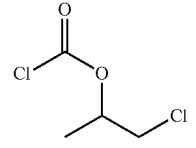 | 15-20 | 90:10 | >99 |
| 2 | 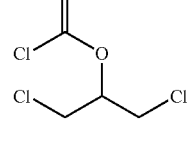 (2.5 mol) | 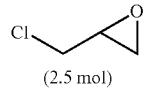 | 15-20 | 98.5:1.5 | 97 |
| 3 | 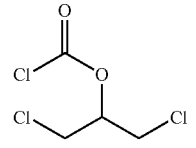 (1.0 mol) | 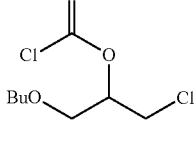 | 15-20 | 96:4 | 96 |
| 4 | 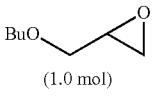 R = C12/C14-n-Alkyl (0.33 mol Epoxid) | 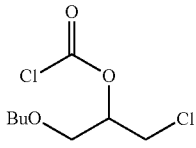 R = C12/C14-n-Alkyl | 15-30 | >98 | >99 |
| 5 | 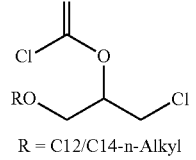 (0.4 mol) | 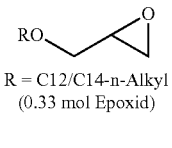 | 35-40 | ca. 95:5 | >99 |

TABLE 1-continued

β-chloro alkylchlorformates

| example | epoxide | β-chloro alkylchlorformates | T [° C.] | selectivity a:b | total yield (a + b) [%] |
|---|---|---|---|---|---|
| 6 |  Polyethylenglycol-diglycidylether, Araldite DY3602 (n = ca. 5) (1 mol Epoxid-Äq.) | 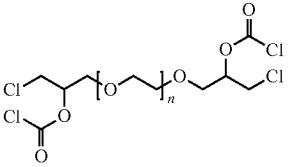 | 10-20 | >95:5 | >99 |

In examples 5 and 6 the yield and selectivity was determined by 1H- and 13C-NMR.

Examples 1 to 6, Second Part: Synthesis of Monothiocarbonates

Synthesis of Compounds with One Cyclic Monothiocarbonate Ring:

The respective β-chloroalkyl chloroformate from examples 1 to 4 (50 g) and dichloromethane (50 mL) are placed in a 500 mL 4 neck round bottom flask equipped with a KPG crescent stirrer, dropping funnel, thermometer and a reflux condenser. The solution was cooled down to 0° C. with an ice bath before $Na_2S$ (1 equiv., 15 wt % aqueous solution) was slowly added, maintaining the temperature at 5° C. After the complete addition the ice bath was removed and the reaction mixture allowed to warm to room temperature. After stirring for 2 h the phases were separated and the aqueous phase was extracted with dichloromethane (2×50 mL). The solvent was removed from the combined organic phases under reduced pressure and the residual liquid purified by (Kugelrohr) distillation, yielding the desired cyclic thiocarbonate.

TABLE 2

Selectivities and isolated yields (purities in brackets) of the various mono-thiocarbonates

| β-chloro alkylchlorformates from example | monothiocarbonate | Area % of GC peak of monothiocarbonate in relation to area of all GC peaks | yield of monithiocarbonate and purity after distillation in brackets |
|---|---|---|---|
| 1 | 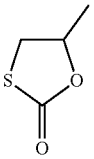 Methyl | 84% | 69% (>97%) |
| 2 | Methylene chloride 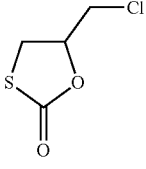 | 86% | 77% (>95%) |
| 3 | $C_4$-Glycidyl 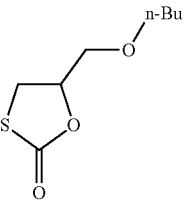 | 92% | 83% (>97%) |

TABLE 2-continued

Selectivities and isolated yields (purities in brackets) of the various mono-thiocarbonates

| β-chloro alkylchlor-formates from example | monothiocarbonate | Area % of GC peak of monothio-carbonate in relation to area of all GC peaks | yield of monithio-carbonate and purity after distillation in brackets |
|---|---|---|---|
| 4 | C$_{12}$/C$_{14}$-Glycidyl 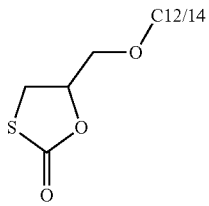 | 66% | 20% (80%) |

Synthesis of Compounds with Two Cyclic Monothiocarbonate Rings:

The respective bis-β-chloroalkyl chloroformiate (50 g) and dichloromethane (50 mL) are placed in a 500 mL 4 neck round bottom flask equipped with a KPG crescent stirrer, dropping funnel, thermometer and a reflux condenser. The solution was cooled down to 0° C. with an ice bath before Na$_2$S (2 equiv., 15 wt % aqueous solution) was slowly added, maintaining the temperature at 5° C. After the complete addition the ice bath was removed and the reaction mixture allowed to warm to room temperature. After stirring for 2 h the phases were separated and the aqueous phase was extracted with dichloromethane (2×50 mL). The solvent was removed from the combined organic phases under reduced pressure yielding the desired cyclic monothiocarbonate.

TABLE 3

Purities of the various compounds with two cyclic monothiocarbonate groups.

| β-chloro alkylchlorformates from example | monothiocarbonate | Purity in % determined by 1H NMR |
|---|---|---|
| 5 | Bisphenol A 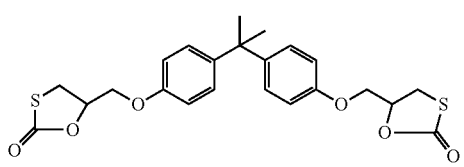 | 80% |
| 6 | PEG 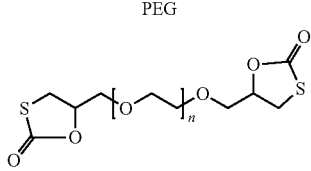 | >99% |

Example 7: Alternative Process to Produce Monothiocarbenate of Example 3, Using NaSH and NaOH Instead of Na$_2$S 1-Chloro-3-butoxy isopropyl chloroformate (20 g) is placed in a 250 mL 4 neck round bottom flask equipped with a KPG crescent stirrer, dropping funnel, thermometer and a reflux condenser. The liquid was cooled down to 0° C. with an ice bath before a solution of NaSH (1 equiv., 15 wt % aqueous solution) containing NaOH (1 equiv.) was slowly added, maintaining the temperature at 5° C. After the complete addition, the ice bath was removed and the reaction mixture allowed to warm to room temperature. The reaction was monitored via GC and after 5 min complete conversion of the chloroformate was observed. The phases were separated and the aqueous phase was extracted with dichloromethane (2×50 mL). The solvent was removed from the combined organic phases under reduced pressure yielding the desired cyclic thiocarbonate in >76% purity.

Example 8: Synthesis of methyacryl-monothiocarbonate

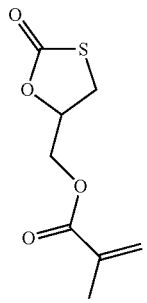

Methacryl-monothiocarbonat

First Step

Glycidylmethacrylate (1 mol) was charged to a reactor and kept at −30° C. 0.008 mol of tetra(n-butyl ammonium chloride were added. Thereafter phosgene is added slowly as the reaction is exothermic. When adding the phosgene the temperature was kept via cooling at the temperature between 13-18° C. The total amount of phosgene was 1.3 mol per 1 mol of epoxide. When the addition of phosgene was completed the reaction mixture was further stirred for about (1.5 hours) while raising the temperature to 25° C. Unreacted phosgene was removed by nitrogen stripping. No further work-up was necessary. The obtained β-chloro alkylchlorformate could be used directly in the next step which is the formation of the monothiocarbonates.

Second Step

The β-chloroalkyl chloroformate obtained (50 g) was placed in a 500 mL 4 neck round bottom flask equipped with a KPG crescent stirrer, dropping funnel, thermometer and a reflux condenser and dichloro-methane (250 g) was added. The liquid was cooled down to 0° C. with an ice bath before Na$_2$S (1 equiv., 15 wt % aqueous solution) was slowly added, maintaining the temperature at 5° C. After the complete addition, the ice bath was removed and the reaction mixture allowed to warm to room temperature. After stirring for 4 h the phases were separated. GC analysis shows an initial purity of the methacryl-monothiocarbonate of 78%. Recrystallization from methanol results in a methacryl-monothiocarbonate with a purity of >98%.

Details of the process are listed in Table 4:

| epoxide | β-chloro alkylchlorformates | Yield Of β-chloro alkylchlorformate (%) | Monothiocarbonate | Yield of monothiocarbonate (%) |
|---|---|---|---|---|
| (1.0 mol) | | 98 | | 75 |

Example 9: Solvent-Free Synthesis

The respective β-chloroalkyl chloroformate from examples 1 or 3 (50 g) were placed in a 250 mL 4 neck round bottom flask equipped with a KPG crescent stirrer, dropping funnel, thermometer and a reflux condenser. The solution was cooled down to 0° C. with an ice bath before $Na_2S$ (1 equiv., 15 weight % aqueous solution) was slowly added, maintaining the temperature at 5° C. After the complete addition the ice bath was removed and the reaction mixture allowed to warm to room temperature. After stirring for 2 h the phases were separated and the aqueous phase was extracted with dichloromethane (2×50 mL). The solvent was removed from the combined organic phases under reduced pressure and the residual liquid purified by distillation, yielding the desired cyclic thiocarbonate.

The invention claimed is:

1. A compound, of formula IVa:

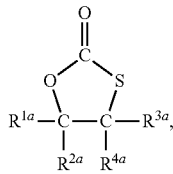

(IVa)

wherein the compound is a mixture of two structural isomeric compounds A and B of formula IVa, wherein isomeric compound A is a compound with $R^{1a}$ being a group $CH_2$—O—$R^6$, $CH_2$—O—C(=O)—$R^7$, or —$CH_2$—$NR^8R^9$, and $R^{2a}$, $R^{3a}$, and $R^{4a}$ are hydrogen, wherein isomeric compound B is a compound with $R^{3a}$ being a group $CH_2$—O—$R^6$, $CH_2$—O—C(=O)—$R^7$, or —$CH_2$—$NR^8R^9$, and $R^{1a}$, $R^{2a}$, and $R^{4a}$ are hydrogen, and wherein the mixture consists of 90 to 99.9% by weight of isomeric compound A and 0.1 to 10% by weight of isomeric compound B, based on a sum of isomeric compounds A and B, and wherein $R^6$ to $R^9$ are a linear or branched alkyl group, alkoxy group, polyalkoxy group, or alkenyl group with at maximum 30 carbon atoms.

2. The compound according to claim 1, wherein in isomeric compound A $R^{1a}$ is a group —$CH_2$—O—$R^6$, —$CH_2$—O—C(=O)—$R^7$, or —$CH_2$—$NR^8R^9$, with $R^6$ to $R^9$ being a $C_1$ to $C_{14}$ alkyl group.

3. The compound according to claim 1, wherein in isomeric compound A the compound of formula IVa is

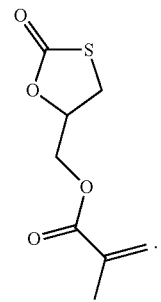

4. The compound according to claim 1, wherein in isomeric compound A, $R^{1a}$ represents $CH_2$—O—C(=O)—$R^7$ and in isomeric compound B, $R^{3a}$ represents $CH_2$—O—C(=O)—$R^7$, wherein $R^7$ is a linear or branched alkyl or alkenyl group.

\* \* \* \* \*